United States Patent [19]

Tanikawa et al.

[11] Patent Number: 5,011,839
[45] Date of Patent: Apr. 30, 1991

[54] 3(2H)PYRIDAZINONES FOR ANTAGONISTIC AGENT AGAINST SRS-A

[75] Inventors: Keizo Tanikawa; Ryozo Saloda, both of Funabashi; Sakuya Tanaka, Minamisaitama; Kenichi Shikada, Saitama, all of Japan

[73] Assignee: Nissan Chemical Industries Ltd., Tokyo, Japan

[21] Appl. No.: 444,953

[22] Filed: Dec. 4, 1989

[30] Foreign Application Priority Data

Dec. 20, 1988 [JP] Japan .................. 63-321476
Oct. 20, 1989 [JP] Japan .................. 1-274661

[51] Int. Cl.$^5$ .................. A61K 31/50; C07D 401/00
[52] U.S. Cl. .................. 514/247; 544/238; 544/239; 544/240; 544/241; 514/252; 514/253
[58] Field of Search .................. 544/238, 239, 240, 241; 514/252, 253, 247

[56] References Cited

U.S. PATENT DOCUMENTS 4,888,423  12/1989  Odarisio .................. 544/238

FOREIGN PATENT DOCUMENTS 0186817  9/1985  European Pat. Off. .......... 544/238
0199281  4/1986  European Pat. Off. .......... 544/238
0275997  1/1988  European Pat. Off. .......... 544/238

Primary Examiner—Mary C. Lee
Assistant Examiner—Robert C. Whittenbaugh
Attorney, Agent, or Firm—Oblon, Spivak, McClelland, Maier & Neustadt

[57] ABSTRACT

A 3(2H)pyridazinone of the formula:

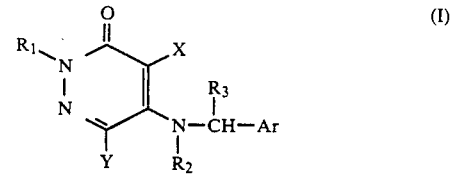

wherein $R_1$ is hydrogen, 2-propenyl, or straight chained or branched $C_1$-$C_4$ alkyl; each of $R_2$ and $R_3$ which may be the same or different, is hydrogen, or straight chained or branched $C_1$-$C_3$ alkyl; X is chlorine, or bromine; Y is hydrogen, halogen, nitro, amino, or —AR$_4$ wherein A is oxygen, or sulfur, and $R_4$ is hydroen, straight chained, branched or cyclic $C_1$-$C_8$ alkyl,

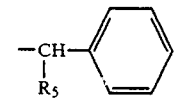

wherein $R_5$ is hydrogen, or straight chained or branched $C_1$-$C_4$ alkyl; and Ar is

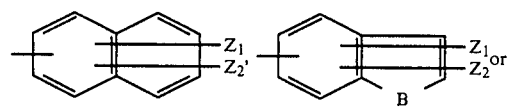

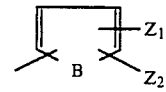

wherein each $Z_1$ and $Z_2$ which may be the same or different, is hydrogen, halogen, straight or branched $C_1$-$C_4$ alkyl, or —OR$_6$ wherein $R_6$ is straight or branched $C_1$-$C_4$ alkyl, and B is oxygen, sulfur, or —N=C— (to form a quinoline or pyridine ring); or a pharmaceutically acceptable salt thereof.

8 Claims, No Drawings

3(2H)PYRIDAZINONES FOR ANTAGONISTIC AGENT AGAINST SRS-A

The present invention relates to novel 3(2H)pyridazinones and pharmaceutically acceptable salts thereof which exhibit antagonism against slow reacting substance of anaphylaxis (SRS-A), processes for their preparation and pharmaceutical compositions containing them as active ingredients.

SRS-A is a chemical mediator released together with histamine, etc. by an allergic reaction and has pharmacological activity to cause a strong and prolonged contraction of bronchial smooth muscle. It has long been known from such a phenomenal aspect. It was found in 1979 that SRS-A itself is a mixture of leukotriene C$_4$ (hereinafter referred to as LTC$_4$), leukotriene D$_4$ (hereinafter referred to as LTD$_4$) and leukotriene E$_4$ (hereinafter referred to as LTE$_4$) [generally called peptide leukotriene]. Extensive researches have been conducted on SRS-A for its relationship with acosmia. As a result, the relationship of SRS-A with immediate type allergic diseases such as bronchial asthma, allergic rhinitis, urticaria and hay fever, has become clear. Further, the relationship of SRS-A with various inflammatory diseases, ischemic heart diseases, etc., has been suggested. Therefore, a compound which exhibits antagonism against SRS-A, is expected to be useful as a prophylactic or thereapeutic drug against the affections caused by either LTC$_4$, LTD$_4$ or LTE$_4$, or by a mixture thereof.

As the antagonists against SRS-A, FPL-55712 (Fisons Limited) and its structural analogues as well as some medicinal substances, have been reported. (Agents and Actions, Vol 9, p. 133-140 (1979), Annual Reports in Medicinal Chemistry, Vol. 20, p. 71-81 (1985) and Agents and Actions, Vol. 18, p. 332-341 (1986)). However, no instance of their practical application has been reported.

Now, the relationship of 3(2H)pyridazinones of the formula I and pharmaceutically acceptable salt thereof according to the present invention with compounds disclosed in published references will be described.

Canadian Patent No. 784,639 (hereinafter referred to as reference (a)) discloses 3(2H)pyridazinone derivatives having hydrogen, C$_1$-C$_8$ alkyl, phenyl or C$_3$-C$_8$ cycloalkyl at 2-position, chlorine or bromine at 4-position and benzylamino at 5-position. However, the reference has no Examples corresponding to the compounds of the present invention, and the application of the compounds disclosed in this reference (a) is restricted to a herbicide, and no mention is made as to their medical use or pharmacological activities.

Chemical Abstract, 62, 2773b, (Bull. Soc. Chim, France, 1964 (9) p 2124-32 (reference (b)) discloses 3(2H)pyridazinones having hydrogen or diethylaminoethyl at 2-position, chlorine at 4-position and benzylamino at 5-position. However, this reference (b) has no Examples corresponding to the compound of the present invention, and it is silent about medical use or pharmacological activities.

German Patent Application No. 1,670,169 published on Nov. 5, 1970 (reference (c)) discloses 3(2)pyridazinones having hydrogen or an aliphatic, cycloaliphatic, araliphatic or aromatic group at 2-position, chlorine or bromine at 4-position and aralkylamino at 5-position. This reference (c) discloses a process for the synthesis of pyridazinones including such compounds, their application to agricultural chemicals, their application as intermediates for medicines or dyestuffs, or their application as intermediates for various compounds. However, no mention is made to their pharmacological activities, and no specific examples are given for such compounds. Further, such compounds are not specifically described.

Angew. Chem. International Edition, Vol. 4, p. 292-300 (1965) (reference (d)) discloses 3(2H)pyridazinones having hydrogen at 2-position, chlorine at 4-position and N-methyl-benzylamino at 5-position. However, this reference (d) has no Examples corresponding to the compounds of the present invention, and no mention is made as to medical use or pharmacological activities.

The present inventors have conducted extensive researches with an object to find compounds which exhibit antagonism against SRS-A. They have found that 5-substituted benzylamino-6-unsubstituted or 6-substituted (2)pyridazinone derivatives having various functional groups and substitution modes, attain the above object, and have already filed patent applications (Japanese Unexamined Patent Publication No. 267560/1986 (reference (e)), Japanese Unexamined Patent Publication No. 0769/1987 (reference (f)) and European Patent 275,997 (reference (g)). However, the compounds disclosed in these references (e), (f) and (g) are all restricted to those wherein the 5-position of the 3(2H)pyridazinone ring is a substituted benzylamino group and contains no other aromatic methylamino group.

The present inventors have then conducted extensive researches on compounds having antagonistic activities against SRS-A, and it has been surprisingly found that (2H)pyridazinones of the formula I and their pharmacologically acceptable salts of the present invention are more excellent in the antagonistic activities against SRS-A than any compounds disclosed in references (a) to (g), and that they are useful as active ingredients for prophylactic or thereapeutic drugs against diseases caused by LTC$_4$, LTD$_4$ or LTE$_4$, or by a mixture thereof which is a component of SRS-A. The present invention has been accomplished on the basis of this discovery.

The present invention provides a 3(2H)pyridazinone of the formula:

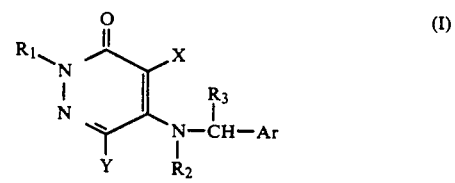

wherein R$_1$ is hydrogen, 2-propenyl, or straight chained or branched C$_1$-C$_4$ alkyl; each of R$_2$ and R$_3$ which may be the same or different, is hydrogen, or straight chained or branched C$_1$-C$_3$ alkyl; X is chlorine, or bromine; Y is hydrogen, halogen, nitro, amino, or —AR$_4$ wherein A is oxygen, or sulfur, and R$_4$ is hydrogen, straight chained, branched or cyclic C$_1$C$_8$ alkyl, or

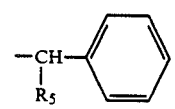

wherein R$_5$ is hydrogen, or straight chained or branched C$_1$-C$_4$ alkyl; and Ar is

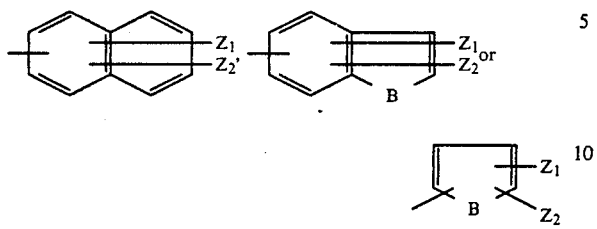

wherein each of Z$_1$ and Z$_2$ which may be the same or different, is hydrogen, halogen, straight or branched C$_1$-C$_4$ alkyl, or —OR$_6$ wherein R$_6$ is straight or branched C$_1$-C$_4$ alkyl, and B is oxygen, sulfur, or —N=C— (to form a quinoline or pyridine ring); or a pharmaceutically acceptable salt thereof.

The present invention provides also processes for their production and pharmaceutical compositions containing them as active ingredients.

Now, the present invention will be described with reference to the preferred embodiments.

Firstly, substituents R$_l$, R$_2$, X, Y, Z$_1$ and Z$_2$ in the compounds of the formula I of the present invention will be described. In the following definitions, "n" means normal, "i" means iso, "sec" means secondary and "t" means tertiary.

Specific Examples of R$_1$ include hydrogen, 2-propenyl, methyl, ethyl, n-propyl, i-propyl, n-butyl, i-butyl, sec-butyl and t-butyl. Among them, preferred is hydrogen, ethyl or i-propyl. More preferred is hydrogen.

Specific examples of R$_2$ and R$_3$ include hydrogen, methyl, ethyl and n-propyl.

Specific examples of X includes chlorine and bromine.

Specific examples of Y include hydrogen, fluorine, chlorine, bromine, iodine, nitro, amino and —AR$_4$.

Here, specific examples of A include oxygen and sulfur.

Specific examples of R$_4$ include hydrogen, methyl, ethyl, n-propyl, i-propyl, n-butyl, i-butyl, sec-butyl, t-butyl, n-pentyl, i-pentyl, sec-pentyl, n-hexyl, i-hexyl, sec-hexyl, n-heptyl, i-heptyl, sec-heptyl, n-octyl, i-octyl, sec-octyl, cyclopropyl, cyclobutyl, cyclopentyl, cyclohexyl, cycloheptyl, cyclooctyl, benzyl, α-methylbenzyl, α-ethylbenzyl, α-n-propylbenzyl and α-n-butylbenzyl.

Preferred specific examples of Y include hydrogen, nitro and —OR$_4$, wherein specific examples of R$_4$ include methyl, ethyl, n-propyl, i-propyl, n-butyl, i-butyl, sec-butyl, t-butyl, n-pentyl, i-pentyl, sec-pentyl, n-hexyl, i-hexyl, sec-hexyl, n-heptyl, i-heptyl, sec-heptyl, n-octyl, i-octyl, sec-octyl, benzyl, α-methylbenzyl, α-ethylbenzyl, α-n-propylbenzyl and α-n-butylbenzyl.

Specific examples of Ar include a naphthalene ring, a benzofuran ring, a benzothiophene ring, a furan ring, a thiophene ring, a quinoline ring and a pyridine ring to which Z$_1$ and Z$_2$ are bonded, wherein specific examples of Z$_1$ and Z$_2$ include, respectively, hydrogen, fluorine, chlorine, bromine, iodine, methyl, ethyl, n-propyl, i-propyl, n-butyl, i-butyl, sec-butyl, t-butyl, methoxy, ethoxy, n-propoxy, i-propoxy, n-butoxy, i-butoxy, sec-butoxy and t-butoxy.

Among the compounds of the formula I of the present invention, preferred are a group of compounds represented by the formula:

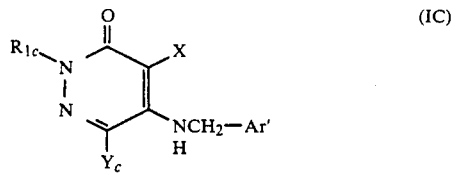

wherein R$_{1c}$ is hydrogen, ethyl, or i-propyl; X is chlorine, or bromine; Y$_c$ is hydrogen, nitro, or —OR'$_4$ wherein R'$_4$ is straight chained, branched or cyclic C$_1$-C$_8$ alkyl, or

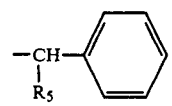

wherein R$_5$ is hydrogen, or straight chained or branched C$_1$-C$_4$ alkyl; and Ar' is

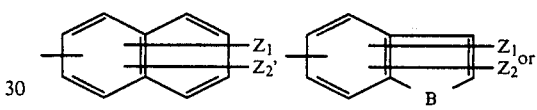

wherein each of Z$_1$ and Z$_2$ which may be the same or different, is hydrogen, halogen, straight or branched C$_1$-C$_4$ alkyl, or —OR$_6$ wherein R$_6$ is straight chained or branched C$_1$-C$_4$ alkyl, and B is oxygen, sulfur, or —N=C—.

The compound of the formula I of the present invention include optical isomers or stereo isomers based on from 1 to 3 asymmetric carbon atoms.

Now, the processes for producing the compounds of the present invention will be described.

3(2H)pyridazinones of the formula I and pharmaceutically acceptable salts thereof according to the present invention can be prepared by the following processes (1) to (5).

Process (1)

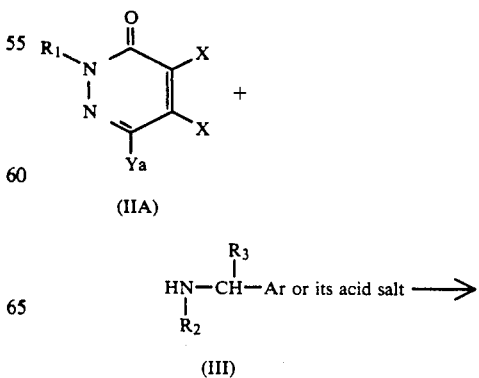

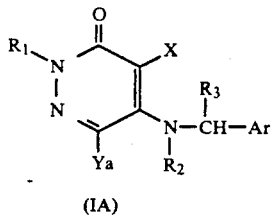

(IA)

In the above formulas, Ya is hydrogen, halogen, nitro, amino or —OR$_4$, and R$_1$, R$_2$, R$_3$, R$_4$, X and Ar are as defined above.

Process (1) comprises reacting a 4,5-dihalo-3(2H)pyridazinone compound of the formula IIA with an arylmethylamine derivative of the formula III or its acid salt in an inert solvent, if necessary, in the presence of a dehydrohalogenating agent to obtain a compound of the formula IA, which has Ya at 6-position, among the compounds of the formula I of the present invention.

In Process (1), a compound of the formula VA:

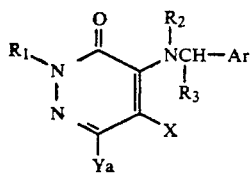

wherein Ya, R$_1$, R$_2$, R$_3$, X and Ar are as defined above, which is a position isomer of the compound of the formula IA having arylmethylamino at 4-position, is formed as a by-product.

The production ratios of the compounds IA and VA depend primarily upon the polarity of the solvent used. Namely, when a solvent of high polarity is used, the production ratio of the compound IA of the present invention tends to be high. Conversely, when a solvent of low polarity such as benzene, toluene or hexane is used, the production ratio of the compound VA tends to be high. Therefore, as a suitable solvent for efficient production of the compound IA of the present invention, an ether solvent such as tetrahydrofuran or 1,4-dioxane, an amide solvent such as formamide, N,N-dimethylformamide, N,N-dimethylacetamide or N-methylpyrrolidone, acetonitrile, dimethylsulfoxide, an alcohol solvent such as methanol, ethanol or propanol, an organic amine solvent such as pyridine, triethylamine, N,N-dimethylaminoethanol or triethanolamine, or water, or a solvent mixture thereof, may be mentioned. The desired compound of the formula IA of the present invention can readily be separated and purified from the mixture of the compounds of the formulas IA and VA by conventional methods known per se in organic synthesis, such as fractional recrystallization or various silica gel chromatography.

During the reaction, hydrogen chloride or hydrogen bromide is generated. It is usually possible to improve the yield by adding to the reaction system a dehydrohalogenating agent which traps such a hydrogen halide.

Any dehydrohalogenating agent may be used so long as it does not adversely affect the reaction and is capable of trapping a hydrogen halide. As such a dehydrohalogenating agent, an inorganic base such as potassium carbonate, sodium carbonate, potassium hydrogencarbonate, or sodium hydrogencarbonate, or an organic base such as N,N-dimethylaniline, N,N-diethylaniline, trimethylamine, triethylamine, N,N-diemthylaminoethanol or pyridine, may be mentioned. Otherwise, the starting material arylmethylamine derivative of the formula III may be used in an excessive amount as the dehydrohalogenating agent. This gives an improved yield in many cases. The reaction temperature may be within a range of from 10° C. to the boiling point of the solvent used for the reaction.

The molar ratio of the starting materials may optionally be set. However, the arylmethylamine derivative of the formula III or its salt may be used usually in an amount of from 1 to 10 moles, preferably from 1.2 to 5 moles, relative to one mole of the 4,5-dihalo-3(2H)pyridazinone derivative of the formula IIA.

The 4,5-dihalo-3(2H)pyridazinone derivative of the formula IIA can be prepared by a conventional process or by an application of a conventional organic reaction as described below. Namely, the compound of the formula IIA wherein Ya is hydrogen, can be prepared by the methods disclosed in the above-mentioned references (e) and (f). Compounds wherein Ya is other than hydrogen can be prepared by the method disclosed in reference (g). Further, among the arylmethylamine derivatives of the formula III and their salts in Process (1), those not available as commercial products can be prepared by the method disclosed in reference (e).

Process (2)

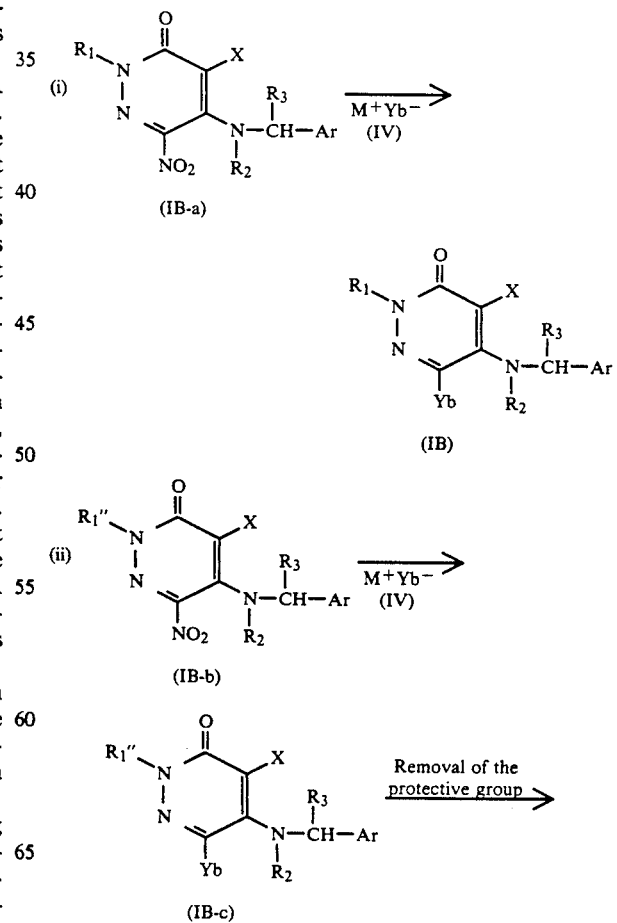

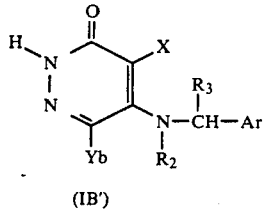

(IB')

In the above formulas, M is alkali metal, Yb is AR$_4$, R$_1''$ is a protective group, and R$_l$, R$_2$, R$_3$, R$_4$, X, Ar and A are as defined above.

Process (2) comprises a substitution reaction of between a 6-nitro-5-arylmethylamino derivative of the formula IB-a or IB-b and an alkali metal salt of the formula IV to obtain a 6-substituted-5-arylmethylamino derivative of the formula IB or IB' of the present invention.

Among the desired compounds, a compound having hydrogen at 2- position of pyridazinone, can be prepared by the direct route as shown in Process 2-(i), or by a route as shown in Process 2-(ii) which comprises converting the 6-nitro derivative of the formula IB-b protected at 2-position with R$_1''$ as a starting material to a compound of the formula IB-c and then removing the protecting group R$_1''$, to obtain the desired compound. The yield is usually better in the latter method in many cases.

As the protective group R$_1''$, tetrahydropyranyl, tetrahydrofuranyl,

2-trimethylsilylethoxymethyl (Me$_3$Si⌒⌒OCH$_2$—), pivaloyloxymethyl(Me$_3$C—CO$_2$CH$_2$—), benzyloxymethyl (C$_6$H$_5$—CH$_2$OCH$_2$—), methoxy (MeOCH$_2$—) or CO$_2$R wherein R is lower alkyl, is preferably used. The removal of the protective group R$_1''$ can easily be conducted by a conventional method for the removal of such protective groups.

Here, the alkali metal of the formula M includes lithium, sodium and potassium.

Therefore, an alkali metal salt of the formula IV used as a nucleophilic agent includes an alkali metal hydroxide, a metal alkoxide, an alkali metal hydrosulfide and a metal mercaptide as defined by above R$_4$.

There is no particular restriction as to the reaction solvent so long as it is inert to the reaction, though it may be suitably selected depending upon the type of the alkali metal salt of the formula IV used for the reaction. In the case of using an alkali metal hydroxide or alkali metal hydrosulfide, the yield can often be improved by using an alcohol solvent such as methanol, ethanol, n-propanol or n-butanol, dimethylsulfoxide, an amide solvent such as formamide, N,N-dimethylformamide or N,N-dimethylaceteamide or a polar solvent such as water. In the case of using a metal alkoxide or metal mercaptide, the reaction is usually conducted in the corresponding alcohol or mercaptan. However, the reaction can be conducted in the above-mentioned ether solvent or in a medium including a benzene solvent such as benzene or toluene.

The reaction temperature varies depending upon the reactants used. It is usually within a range of from $-15°$ C. to the boiling point of the solvent used for the reaction.

The molar ratio of the starting materials can be optionally determined, and it is sufficient that the alkali metal salt of the formula IV is used in an amount of from 1.2 to 10 mols relative to one mol of the 6-nitro-5-arylmethylamino derivative of the formula IB-a or IB-b.

The desired compound can readily be isolated and purified by a method known per se in organic syntheses such as recrystallization, various silica gel chromatography or distillation.

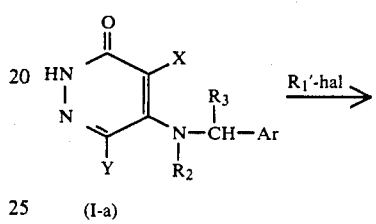

(I-a)

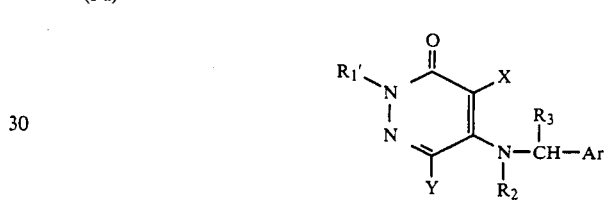

(I-b)

Process (3)

In the above formulas, R$_1'$ is 2-propenyl, or straight chained or branched C$_1$-C$_4$ alkyl, hal is chlorine, bromine, or iodine, and R$_2$, R$_3$, X, Y and Ar are as defined above.

Process (3) is a process which comprises reacting a compound of the formula I-a i.e. a compound of the formula I having hydrogen at 2-position of pyridazinone, with a halogeno derivative of the formula R$_1'$-hal, to obtain a 2-substituted compound of the formula I-b.

Process (3) is usually conducted in the presence of an inorganic base such as potassium carbonate, sodium carbonate, lithium carbonate, potassium hydrogencarbonate, sodium hydrogencarbonate or lithium hydroxide. Further, in the case where R$_2$ is alkyl in the formula I-a, it is possible to use a metal hydride such as sodium hydride or n-butyl lithium in addition to the above inorganic base.

In the case of using the inorganic base, a ketone solvent such as acetone, methyl ethyl ketone or diethyl ketone, an amide solvent such as formamide, N,N-dimethylformamide or N,N-dimethylaceteamide, an alcohol solvent such as methanol or ethanol, or water, or a mixture thereof, is preferred as the reaction solvent, and in the case of using the metal hydride, an ether solvent is preferably used.

In the case of using the inorganic base, the reaction temperature is usually within a range of from 0° C. to the boiling point of the solvent, and in the case of using the metal hydride, it is usually within a range of from $-78°$ to 60° C.

The molar ratio of the starting materials may optionally be determined. However, the halogen compound of the formula R₁-hal is used usually in an amount of from 1 to 5 mols relative to one mol of the compound of the formula I-a.

The desired compound can be isolated and purified in accordance with the method as described with respect to Process (2).

Process (4)

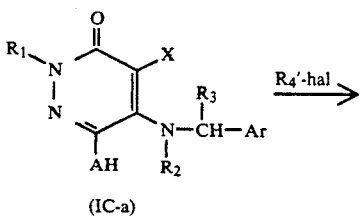

(IC-a)

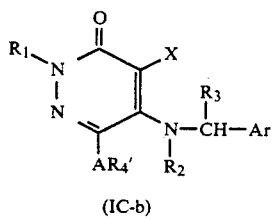

(IC-b)

In the above formulas, R₁, R₂, R₃, R₄′, X, Ar and hal are as defined above.

Process (4) is a process which comprises reacting a 6-hydroxy or 6-mercapto derivative of the formula IC-a with a halogeno derivative of the formula R₄′-hal, to obtain a 6-alkoxy or 6-substituted mercapto derivative of the formula IC-b of the present invention.

For Process (4), it is possible to employ reaction conditions similar to those in the above Process (3).

Process (5)

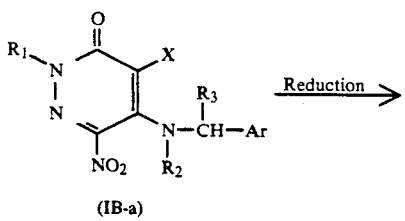

(IB-a)

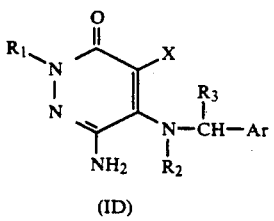

(ID)

In the above formulas, R₁, R₂, R₃, X and Ar are as defined above.

Process (5) is a process which comprises a reduction reaction of a 6-nitro derivative of the formula IB-a, to obtain a 6-amino derivative of the formula ID of the present invention.

For the reduction, a method of using sodium hydrosulfite, sodium sulfide or the like, or a method of using a metal such as iron, zinc, tin or the like in the presence of acid, may be employed. For this reduction reaction, it is desired to avoid a high temperature or a strong acidic condition with a high concentration of an acid, because a functional group such as halogen or arylmethyl, in the compound IB-a, will readily be reduced or eliminated under a strong acidic condition.

A protic solvent such as methanol, ethanol, n-propanol, acetic acid or water, or a mixture thereof, is usually preferably used as the solvent for the reaction. The reaction temperature may usually be within a range of from −10° to 50° C. The reaction usually smoothly.

As the manner of administration of the 3(2H)pyridazinones of the formula I or their pharmaceutically acceptable salts of the present invention, there may be mentioned a non-oral administration by injection (subcutaneous, intravenous, intramuscular or intraperitoneal injection), an ointment, a suppository or an aerosol, or an oral administration in the form of tablets, capsules, granules, pills, syrups, liquids, emulsions or suspension.

The above pharmacological or veterinary composition contains a compound of the present invention in an amount of from about 0.1 to about 99.5% by weight, based on the total weight of the composition. To the compound of the present invention or to the composition containing the compound of the present invention, other pharmacologically or veterinarily active compounds may be incorporated. Further, the composition of the present invention may contain a plurality of compounds of the present invention.

The clinical dose of the compound of the present invention varies depending upon the age, the body weight, the sensitivity or the symptom, etc. of the patient. However, the effective daily dose is usually from 0.003 to 1.5 g, preferably from 0.01 to 0.6 g, for an adult. However, if necessary, an amount outside the above range may be employed.

The compounds of the present invention may be formulated into various suitable formulations depending upon the manner of administration, in accordance with conventional methods commonly employed for the preparation of pharmaceutical formulations.

Namely, tablets, capsules, granules or pills for oral administration, may be prepared by using an excipient such as sugar, lactose, glucose, starch or mannitol; a binder such as syrups, gum arabic, gelatin, sorbitol, tragacant gum, methyl cellulose or polyvinylpyrrolidone; a disintegrant such as starch, carboxymethyl cellulose or its calcium salt, crystal cellulose powder or polyethylene glycol; a gloss agent such as talc, magnesium or calcium stearate or colloidal silica; or a lubricant such as sodium laurate or glycerol. The injections, solutions, emulsions, suspensions, syrups or aerosols, may be prepared by using a solvent for the active ingredient such as water, ethyl alcohol, isopropyl alcohol, propylene glycol, 1,3-butyl glycol, or polyethylene glycol; a surfactant such as a sorbitol fatty acid ester, a polyoxyethylene fatty acid ester, a polyoxyethylene ether of hydrogenated caster oil or lecithin; a suspending agent such as a sodium salt of carboxymethyl cellulose, a cellulose derivative such as methyl cellulose, or a natural rubber such as tragacant gum or gum arabic; or a preservative such as a paraoxy benzoic acid ester, benzalkonium chloride or a salt of sorbic acid. Likewise, the suppositories may be prepared by using e.g. polyethylene glycol, lanolin or coconut butter.

Now, the present invention will be described in detail with reference to Examples including Preparation Examples, Formulation Examples and Test Examples. However, it should be understood that the present invention is by no means restricted by these specific Examples. In Preparation Examples or in Table 5, the symbols "NMR", "IR" and "MS" indicate "nuclear magnetic resonance spectrum", "infrared spectrum" and "mass spectrometry", respectively. IR was measured by the potassium bromide disk method, and NMR was measured in heavy chloroform, unless otherwise specified. In the MS data in Table 1, only the principal peaks or typical fragment peaks are given.

PREPARATION EXAMPLE 1

4-Chloro-5-(4-methoxy-1-naphthylmethylamino)-3(2H)pyridazinone (Compound No. 5)

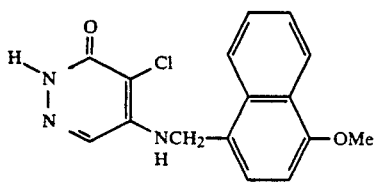

A mixture comprising 330 mg of 4,5-dichloro-3(2H)pyridazinone, 1.12 g of 4-methoxy-1-naphthylmethylamine and 30 ml of ethanol, was refluxed under stirring overnight. The solvent was evaporated under reduced pressure, and a mixture of ethyl acetate and ethyl ether was poured to the residue, whereupon precipitated crystals were collected by filtration. The product was recrystallized from a mixture of methanol/water to obtain 410 mg of the above identified command as slightly yellow crystals having a melting point of from 265° to 266° C.

NMR(CDCl$_3$+DMSO-d$_6$).
$\sigma$:8.2–7.2(5H,m),7.55(1H,s), 7.0–6.4(1H,broad s),6.77(1H,d), 4.9 0 (2H,d),3.95(3H,s).
MS(m/e):314(M+), 280,171(100%).

PREPARATION EXAMPLE 2

2Ethyl-4-bromo-5-(2-furanylmethylamino)-3(2H)pyridazinone (Compound No. 22)

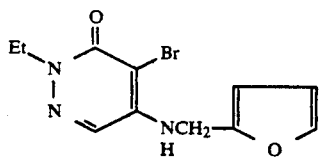

A mixture comprising 564 mg of 2-ethyl-4,5-dibromo-3(2H)pyridazinone, 291 mg of 2-furanylmethylamine, 530 mg of sodium carbonate, 15 ml of water and 15 ml of 1,4-dioxane, was refluxed under stirring for 5 hours. The solvent was distilled off under reduced pressure, and water was poured to the residue thus obtained. The mixture was extracted with ethyl acetate. The extract was washed with water and dried over sodium sulfate. Then, the solvent was distilled off. The residue oily substance thus obtained was purified by silica gel column chromatography by using a mixture of benzene/ethyl acetate (volume ratio of 2/1) as developer to obtain 294 mg of the above identified compound as colorless crystals having a melting point of from 120° to 123° C. (as recrystallized from a mixture of ethyl acetate/ethyl ether/n-hexane).

NMR. $\sigma$:7.51(1H,s),7.32(1H,d),6.35–6.15(2H,m), 5.3–4.9(1H,broad s),4.45(2H,d), 4.14(2H,q),1.33(3H,t). MS(m/e):297(M+),218,190,81(100%).

PREPARATION EXAMPLE 3

2-i-propyl-4-bromo-5-(2-methoxy-1-naphthylmethylamino)-3(2H)pyridazinone (Compound No. 26)

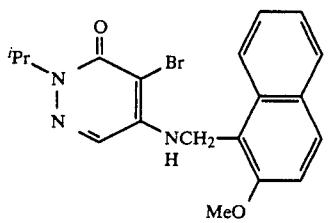

A mixture comprising 1.48 g of 2-i-propyl-4,5-dibromo-3(2H)pyridazinone, 1.68 g of 2-methoxy-1-naphthylmethylamine hydrochloride, 1.33 g of sodium carbonate, 30 ml of water and 30 ml of 1,4-dioxane, was refluxed under stirring overnight. Then, the solvent was distilled off under reduced pressure, and water was poured to the residue thus obtained. The mixture was extracted with ethyl acetate. The extract was washed sequentially with a 2 wt% hydrochloric acid aqueous solution, water and a saturated sodium chloride aqueous solution and then dried over sodium sulfate. Then, the solvent was distilled off. The residual solid thus obtained was crystallized from ethyl acetate/n-hexane to obtain 1.18 g of the above identified compound as colorless crystals having a melting point of from 160° to 161° C.

NMR. $\sigma$:8.1–71.(7H,m),5.6–4.8(2H,m),4.95(2H,d), 3,98(3H,s),1.30(6H,d).
MS(m/e):401(M+),322,171(100%),141.

PREPARATION EXAMPLE 4

4-Chloro-5-(4-methoxy-1-naphthylmethylamino)-6-nitro-3(2H)pyridazinone (Compound No. 30)

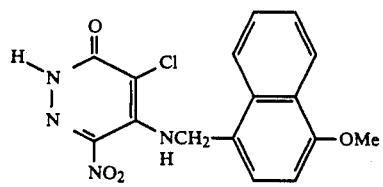

A mixture comprising 1.00 g of 4,5-dichloro-6-nitro-3(2H)pyridazinone, 2.67 g of 4-methoxy-1-naphthylamino and 50 ml of ethanol, was refluxed under stirring overnight. After cooling, precipitated crystals were collected by filtration. The product was dissolved in ethyl acetate, treated by silica gel and then recrystallized from ethyl acetate/ethyl ether to obtain 1.08 g of the above identified compound as yellowish orange crystals having a melting point of from 218° to 220° C.

NMR(CDCl$_3$+DMSO-d$_6$). $\sigma$:8.4–7.2(5H,m),7-.2–6.7(1H,broad s), 6.74(1H,d),5.06(2H,d),3.93(3H,s). MS(m/e):360(M+),325,171(100%).

PREPARATION EXAMPLE 5

2-Ethyl-4-chloro-5-(4-methoxy-1-naphthylmethylamino)-6-nitro-3(2H)pyridazinone (Compound No. 37)

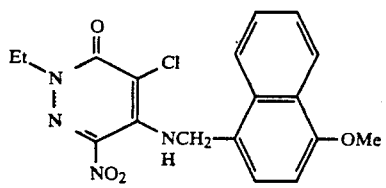

A mixture comprising 100 mg of 4-chloro-5-(4-methoxy-1-naphthylmethylamino)-6-nitro-3(2H)pyridazinone (Compound No. 30) prepared in Preparation Example 4, 218 mg of ethyl iodide, 193 mg of potassium carbonate and 30 ml of methyl ethyl ketone, was refluxed under stirring for 1.5 hours. The reaction mixture was filtered, and the solvent of the filtrate was distilled off under reduced pressure. Water was poured to the residue thus obtained, and the mixture was extracted with benzene. The extract was washed with water and with a saturated sodium chloride aqueous solution and dried over sodium sulfate. Then, the solvent was distilled off to obtain 110 mg of the above identified compound as a slightly yellow brown caramel substance.

NMR. $\sigma$:8.9–7.1(5H,m),6.7–6.3(1H,broad s), 6.66(1H,d),5.03(2H,d),4.17(2H,q), 3.93(3H,s),1.38(3H,t).
MS(m/e):388(M+),353,171(100%).

PREPARATION EXAMPLE 6

4-Bromo-5-(2-n-propoxy-1-naphthylmethylamino)-6-amino-3(2H)pyridazinone (Compound No. 46)

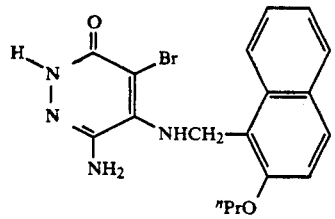

500 mg of 4-bromo-5-(2-n-propoxy-1-naphthylmethylamino)-6-nitro-3(2H)pyridazinones (Compound No. 45) was dissolved in a mixture comprising 50 ml of ethanol and 25 ml of a 10% sodium carbonate aqueous solution. Then, 1.40 g of sodium hydrosulfite was gradually added under stirring, and the mixture was stirred at room temperature for 1 hour and then the reaction solution was left to stand overnight. Glacial acetic acid was dropwise added to neutralize the reaction solution. Then, the solvent was distilled off under reduced pressure. Water was poured to the residue thus obtained, and the mixture was extracted with chloroform. The extract was washed sequentially with water and with a saturated sodium chloride aqueous solution and then dried over sodium sulfate. The solvent was distilled off to obtain a yellowish orange solid substance. This product was purified by silica gel column chromatography by using chloroform and a mixture of chloroform/methanol (volume ratio of 20/1) as developers to obtain 160 mg of the above identified compound as colorless crystals having a melting point of from 199° to 203° C. (as recrystallized from chloroform/ethyl ether) from the fraction eluted with the mixture of chloroform/ethanol (volume ratio of 20/1).

NMR(CDCl$_3$+DMSO-d$_6$).
$\sigma$:8.1–7.1(6H,m),5.12(2H,d),4.07(2H,t), 1.02(3H,t).
MS(m/e):402(M+),323,199(100%),157.

PREPARATION EXAMPLE 7

2-Ethyl-4-bromo-5-(2-n-propoxy-1-naphthylmethylamino)-6-amino-3(2H)pyridazinone (Compound No. 49)

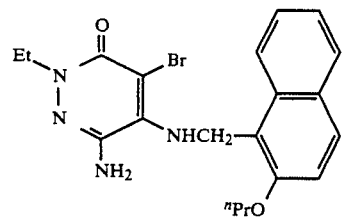

(i) A mixture comprising 50 mg of 4-bromo-5-(2-n-propoxy-1-naphthylmethylamino)-6-amino-3(2H)pyridazinone (Compound No. 46) prepared in Preparation Example 6, 94 mg of ethyl iodide, 83 mg of potassium carbonate, 20 ml of methyl ethyl ketone and 1 ml of N,N-dimethylformamide, refluxed under stirring for 1.5 hours. Then, the solvent was distilled off under reduced pressure, and water was poured to the residue thus obtained. The mixture was extracted with benzene. The extract was washed with water and with a saturated sodium chloride aqueous solution and then dried over sodium sulfate. Then, the solvent was distilled off. The residual solid substance was purified by silica gel column chromatography by using chloroform and a mixture of chloroform/methanol (volume ratio of 10/1) as developers, to obtain 15 mg of the above identified compound as colorless crystals having a melting point of from 144° to 145° C. (as recrystallized from chloroform/ethyl ether/hexane).

NMR. $\sigma$:8.0–7.1(6H,m),4.94(2H,d),4.31(2H,broad s), 4.13(2H,q),3.95(2H,t),1.27,1.06 (each 3H,t).
MS(m/e):430(M+),351,199(100%),157,129.

IR($\nu_{max}^{KBr}$)cm$^{-1}$:

3340,3210,1620(shoulder), 1600,1515,1420.

(ii) 530 mg of 2-ethyl-4-bromo-5-(2-n-propoxy-1-naphthylmethylamino)-6-nitro-3(2H)pyridazinone (Compound No. 48) was dissolved in a mixture comprising 50 ml of ethanol and 25 ml of a 10 wt% sodium carbonate aqueous solution. Then, 1.0 g of sodium hydrosulfite was gradually added under stirring, and the mixture was then stirred at room temperature for 2.5 hours. Glacial acetic acid was added to neutralize the reaction solution. Then, the solvent was distilled off under reduced pressure. Water was poured to the residue thus obtained, and the mixture was extracted with chloroform. The extract was washed sequentially with water and with a saturated sodium chloride aqueous solution and then dried over sodium sulfate. Then, the solvent was distilled off to obtain a residual yellowish orange solid substance. This product was purified by silica gel column chromatography by using chloroform and a mixture of chloroform/methanol (volume ratio of

PREPARATION EXAMPLE 8

4-Chloro-5-(4-methoxy-1-naphthylmethylamino)-6-i-propoxy-3(2H)pyridazinone (Compound No. 32)

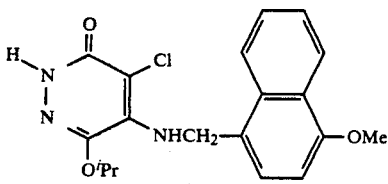

A mixture comprising 350 mg of 4,5 dichloro 6-1-propoxy-3(2H)pyridazinone, 1.23 g of 4-methoxy-1-naphthylmethylamine and 30 ml of a mixture of water/1,4-dioxane (volume ratio of 1/1), was refluxed under stirring for 3.5 hours. The reaction mixture was concentrated, and precipitated crystals were collected by filtration and recrystallized from a mixture of methanol/water to obtain 420 mg of the above identified compound as colorless crystals having a melting point of from 244° to 247° C.

NMR(CDCl$_3$-DMSO-d$_6$).
$\sigma$:8.4–7.2(5H,m),6.67(1H,d),5.70(1H,broad s), 5.17(2H,d),3.95(3H,s),1.12(6H,d).
MS(m/e):373(M+),338,171(100%).

PREPARATION EXAMPLE 9

2-Ethyl-4-chloro-5-(4-methoxy-1-naphthylmethylamino)-6-i-propoxy-3(2H)pyridazinone (Compound No. 40)

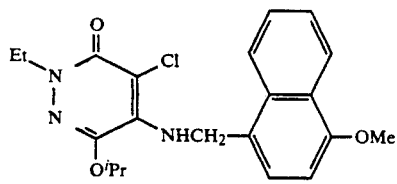

(i) A mixture comprising 150 mg of 4-chloro-5-(4-methoxy-1-naphthylmethylamino)-6-i-propoxy-3(2H)pyridazinone prepared in Preparation Example 8, 310 mg of ethyl iodide, 280 mg of potassium carbonate, 30 ml of methyl ethyl ketone, and 2 ml of N,N-dimethylformamide, was refluxed under stirring for 1.5 hours. The reaction mixture was filtered, and the solvent of the filtrate was distilled off under reduced pressure. Water was poured to the residue thus obtained, and the mixture was extracted with benzene. The extract was washed with a saturated sodium chloride aqueous solution and dried over sodium sulfate. Then, the solvent was distilled off. The residual oily substance thus obtained was purified by silica gel column chromatography. Elution was conducted with a mixture of benzene/ethyl acetate (volume ratio of 3/1), and crystallization was further conducted from ethyl ether/n-hexane to obtain 110 mg of the above identified compound as colorless crystals with a melting point of from 118.5° to 120° C.

NMR. $\sigma$:8.5–7.2(5H,m),6.65(1H,d),5.12(2H,d), 4.01(2H,q),3.90(3H,s),1.29(3H,t), 1.18(6H,d).
MS(m/e):401(M+),366,171(100%).

(ii) 150 mg of 2-ethyl-4-chloro-5-(4-methoxy-1-naphthylamino)-6-nitro-3(2H)pyridazinone (Compound No. 37) prepared in Preparation Example 5 was dissolved in 5 ml of i-propanol. While stirring the solution, a solution having 30 mg of sodium dissolved in 5 ml of i-propanol under heating, was dropwise added. After the dropwise addition, the reaction mixture was stirred at room temperature overnight. Water was poured to the reaction solution, and the mixture was extracted with chloroform. The extract was washed sequentially with water and a saturated sodium chloride aqueous solution and then dried over sodium sulfate. Then, the solvent was distilled off. The residual oily substance thus obtained was purified by silica gel column chromatography (developer: benzene/ethyl acetate=5-3/1) to obtain 20 mg of the above identified compound. The behavior on a silica gel thin layer chromatography and NMR and MS spectrum data of this product were identical with those of the product obtained in the above method (i).

PREPARATION EXAMPLE 10

4,6-Dichloro-5-(4-methoxy-1-naphthylmethylamino)-3(2H)pyridazinone (Compound No. 34)

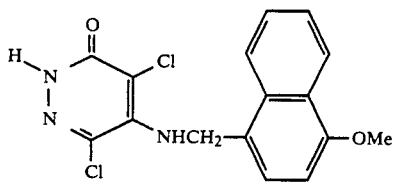

A mixture comprising 800 mg of 4,5,6-trichloro-3(2H)pyridazinone, 2.68 g of 4-methoxy-1-naphthylmethylamine and 10 ml of ethanol, was refluxed under stirring for 4 hours. After cooling, precipitated crystals were collected by filtration. Then, the product was dissolved in hot ethyl acetate and treated by silica gel. The filtrate was concentrated, and precipitated crystals were collected by filtration to obtain 330 mg of the above identified compound as colorless crystals having a melting point of from 228° to 231° C.

NMR(CDCl$_3$+DMSO-d$_6$).
$\sigma$:8.4–7.2(5H,m),6.72(1H,d),5.18(2H,d), 3.95(3H,s).
MS(m/e):349(M+),314,171(100%).

PREPARATION EXAMPLE 11

4-Chloro-5-(3-pyridylmethylamino)-6-i-propoxy-3(2H)pyridazinone hydrochloride (Compound No. 51)

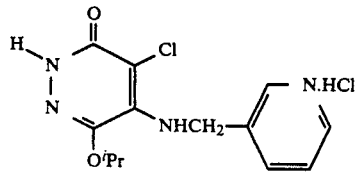

2.32 g of 4-chloro-5-(3 pyridylmethylamino)-6-i-propoxy-3(2H)pyridazinone prepared in the same manner as in Preparation Example 8, was dissolved in a 10% hydrogen chloride methanol solution, and the solution was stirred at room temperature for 1.5 hours. The solvent was distilled off under reduced pressure, and the obtained residue was crystallized from methanol/-diethyl ether, to obtain 2.55 g of the above identified compound as colorless crystals having a melting point of from 232° to 234° C.

MS(m/e):294(M+-HCl),252(100%),217,92.

Compounds prepared in the synthetic manner similar to those in the above Preparation Examples are shown in Table I. In the right hand end column in the Table, the number of the Example employed is indicated.

Further, 3(2H)pyridazinones of the formula I and their pharmaceutically acceptable salts of the present invention include compounds listed in Table II in addition to those described in the above Preparation Examples and in Table I.

In Tables I and II, n means "normal", i means "iso", sec means "secondary", Me means "a methyl group", Et means "an ethyl group", Pr means "a propyl group", Bu menas "a butyl group", Pen means "a pentyl group", Hex means "a hexyl group", Hep means "a heptyl group", Oct means "an octyl group", and Ph means "a phenyl group".

TABLE I

| Compound No. | $R_1$ | $R_2$ | $R_3$ | X | Y | Ar | m.p. (°C.) | MS(m/c) | Example No. |
|---|---|---|---|---|---|---|---|---|---|
| 1 | H | H | H | Cl | H | 2-furyl | 170~172 | 225(M+), 81(100%) | 1 |
| 2 | H | H | H | Cl | H | 1-naphthyl | 233~235 | 285(M+), 141(100%) | 1 |
| 3 | H | H | H | Cl | H | 2-naphthyl | 249~252 | 285(M+), 141(100%) | 1 |
| 4 | H | H | H | Cl | H | 2-MeO-naphthyl | 248~252 | 315(M+), 171(100%) | 1 |
| 5 | H | H | H | Cl | H | 4-MeO-naphthyl | 265~266 | See Preparation Example 1 | 1 |
| 6 | H | H | H | Cl | H | 2-nPrO-naphthyl | 215~217 | 343(M+), 157(100%) | 1 |
| 7 | H | H | H | Cl | H | 2-thienyl | 208~210 | 241(M+), 97(100%) | 1 |
| 8 | H | H | H | Cl | H | 3-Me-2-thienyl | 203~205 | 255(M+), 111(100%) | 1 |
| 9 | H | H | H | Cl | H | 5-Me-2-thienyl | 174~175 | 255(M+), 111(100%) | 1 |

TABLE I-continued
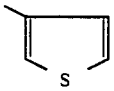
| Compound No. | R₁ | R₂ | R₃ | X | Y | Ar | m.p. (°C.) | MS(m/c) | Example No. |
|---|---|---|---|---|---|---|---|---|---|
| 10 | H | H | H | Cl | H | 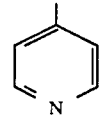 | 230~235 | 241(M⁺), 97(100%) | 1 |
| 11 | H | H | H | Cl | H | 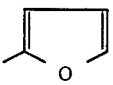 | 252~256 | 236(M⁺), 92(100%) | 1 |
| 12 | H | H | H | Br | H | 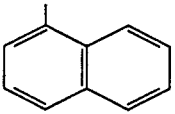 | 162~165 | 269(M⁺), 81(100%) | 1 |
| 13 | H | H | H | Br | H | 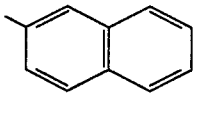 | 258~262 | 329(M⁺), 141(100%) | 1 |
| 14 | H | H | H | Br | H | 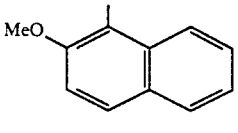 | 238~242 | 329(M⁺), 141(100%) | 1 |
| 15 | H | H | H | Br | H | 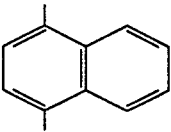 | 210~214 | 359(M⁺), 171(100%) | 1 |
| 16 | H | H | H | Br | H | 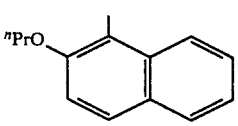 | 223~224 | 359(M⁺), 171(100%) | 1 |
| 17 | H | H | H | Br | H | 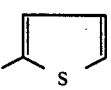 | 193~195 | 387(M⁺), 157(100%) | 1 |
| 18 | H | H | H | Br | H | 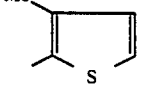 | 203~205 | 285(M⁺), 97(100%) | 1 |
| 19 | H | H | H | Br | H | 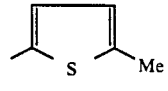 | 194~196 | 299(M⁺), 111(100%) | 1 |
| 20 | H | H | H | Br | H |  | 176~178 | 299(M⁺), 111(100%) | 1 |

TABLE I-continued

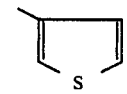

| Compound No. | R₁ | R₂ | R₃ | X | Y | Ar | m.p. (°C.) | MS(m/c) | Example No. |
|---|---|---|---|---|---|---|---|---|---|
| 21 | H | H | H | Br | H | 3-thienyl | 214~217 | 285(M$^+$), 97(100%) | 1 |
| 22 | Et | H | H | Br | H | 2-furyl | 120~123 | See Preparation Example 2 | 2 |
| 23 | Et | H | H | Br | H | 1-naphthyl | 251~255 | 357(M$^+$), 141(100%) | 2 |
| 24 | Et | H | H | Br | H | 2-naphthyl | 174~176 | 357(M$^+$), 141(100%) | 3 |
| 25 | Et | H | H | Br | H | 2-MeO-1-naphthyl | 168~170 | 387(M$^+$), 171(100%) | 3 |
| 26 | $^i$Pr | H | H | Br | H | 2-MeO-1-naphthyl | 160~161 | See Preparation Example 3 | 3 |
| 27 | H | Me | H | Cl | H | 2-MeO-1-naphthyl | 235~238 | 329(M$^+$), 171(100%) | 1 |
| 28 | H | Me | H | Br | H | 2-MeO-1-naphthyl | 212~214 | 294(M$^+$—Br), 171(100%) | 1 |
| 29 | H | Me | H | Cl | NO₂ | 2-MeO-1-naphthyl | 203~205 | 374(M$^+$), 171(100%) | 4 |
| 30 | H | H | H | Cl | NO₂ | 4-MeO-1-naphthyl | 218~220 | See Preparation Example 4 | 4 |

TABLE I-continued

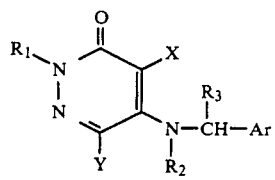

| Compound No. | $R_1$ | $R_2$ | $R_3$ | X | Y | Ar | m.p. (°C.) | MS(m/c) | Example No. |
|---|---|---|---|---|---|---|---|---|---|
| 31 | H | H | H | Cl | OEt | 4-OMe-naphthyl | 250~253 | 359($M^+$), 171(100%) | 8 |
| 32 | H | H | H | Cl | O$^i$Pr | 4-OMe-naphthyl | 244~247 | See Preparation Example 8 | 8 |
| 33 | H | H | H | Cl | O$^i$Pr | 2-$^n$PrO-naphthyl | 159~162 | 401($M^+$), 199(100%) | 8 |
| 34 | H | H | H | Cl | Cl | 4-OMe-naphthyl | 228~231 | See Preparation Example 10 | 10 |
| 35 | H | H | H | Cl | Cl | 2-$^n$PrO-naphthyl | 179~198.5 | 377($M^+$), 199(100%) | 10 |
| 36 | H | H | H | Cl | O$^i$Pr | 4-pyridyl | 237~240 | 294($M^+$), 92(100%) | 8 |
| 37 | Et | H | H | Cl | $NO_2$ | 4-OMe-naphthyl | Caramel-like | See Preparation Example 5 | 5 |
| 38 | Et | H | H | Cl | OMe | 4-OMe-naphthyl | 135~137 | 373($M^+$), 171(100%) | 9-ii) |

TABLE I-continued

[Structure:]

$$R_1-N(-N=)-C(=O)-C(X)=C(N(R_2)-CH(R_3)-Ar)-C(Y)=$$ (pyridazinone ring with R1 on N, X, Y, and N-CH(R3)-Ar substituents)

| Compound No. | R₁ | R₂ | R₃ | X | Y | Ar | m.p. (°C.) | MS(m/c) | Example No. |
|---|---|---|---|---|---|---|---|---|---|
| 39 | Et | H | H | Cl | OEt | 4-OMe-naphthyl | 131.5~133.5 | 387(M⁺), 171(100%) | 9-ii) |
| 40 | Et | H | H | Cl | OiPr | 4-OMe-naphthyl | 118~120 | See Preparation Example 9 | 9 |
| 41 | iPr | Me | H | Cl | NO₂ | 2-OMe-naphthyl | Oily | 416(M⁺), 171(100%) | 5 |
| 42 | iPr | H | H | Cl | NO₂ | 4-OMe-naphthyl | 147~148.5 | 402(M⁺), 171(100%) | 5 |
| 43 | iPr | H | H | Cl | OiPr | 4-OMe-naphthyl | 119~121 | 415(M⁺), 171(100%) | 9-ii) |
| 44 | H | H | H | Br | NO₂ | 3-Me-2-thienyl | 128~134 | 344(M⁺), 111(100%) | 4 |
| 45 | H | H | H | Br | NO₂ | 2-nPrO-naphthyl | 175~178 | 432(M⁺), 199(100%) | 4 |
| 46 | H | H | H | Br | NH₂ | 2-nPrO-naphthyl | 199~203 | See Preparation Example 6 | 6 |
| 47 | H | H | H | Br | NO₂ | 4-OMe-naphthyl | 212~215 | 404(M⁺), 171(100%) | 4 |

TABLE I-continued $$\text{structure with } R_1\text{-N, N=N, C=O, X, Y, and } N(R_2)\text{-CH}(R_3)\text{-Ar substituents on pyridazinone ring}$$

| Compound No. | R₁ | R₂ | R₃ | X | Y | Ar | m.p. (°C.) | MS(m/c) | Example No. |
|---|---|---|---|---|---|---|---|---|---|
| 48 | Et | H | H | Br | NO₂ | 1-methyl-2-nPrO-naphthyl | | 406(M⁺), 199(100%) | 5 |
| 49 | Et | H | H | Br | NH₂ | 1-methyl-2-nPrO-naphthyl | 144~145 | See Preparation Example 7 | 7 |
| 50 | Et | H | H | Br | NO₂ | 1-methyl-4-OMe-naphthyl | Oily | 432(M⁺), 171(100%) | 5 |
| 51 | H | H | H | Cl | O^iPr | 5-methyl-pyridyl·HCl | 232~234 | See Preparation Example 11 | 11 |
| 52 | H | H | H | Cl | H | 3-methyl-pyridyl | 255~257 | 236(M⁺), 92(100%) | 1 |
| 53 | H | H | H | Cl | OEt | 3-methyl-pyridyl | 229~232 | 280(M⁺), 92(100%) | 8 |
| 54 | H | H | H | Cl | O^nBu | 3-methyl-pyridyl | 159~160 | 308(M⁺), 92(100%) | 8 |
| 55 | H | H | H | Cl | O^nBu | 5-methyl-pyridyl·HCl | 178~184 | 308(M⁺—HCl), 217 (100%) | 11 |
| 56 | H | H | H | Cl | O^nBu | 5-methyl-2-OMe-pyridyl | 141~142 | 338(M⁺), 122(100%) | 8 |
| 57 | H | H | H | Cl | O^nBu | 5-methyl-2-Cl-pyridyl | 207~209 | 342(M⁺), 126(100%) | 8 |

TABLE I-continued
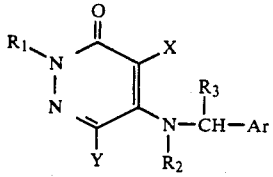
| Compound No. | R₁ | R₂ | R₃ | X | Y | Ar | m.p. (°C.) | MS(m/c) | Example No. |
|---|---|---|---|---|---|---|---|---|---|
| 58 | H | H | H | Cl | O$^n$Pen | 3-pyridyl | 148~149.5 | 322 322(M$^+$), 92(100%) | 8 |
| 59 | H | H | H | Cl | O$^n$Pen | 3-pyridyl·HCl | 171~178 | 322(M$^+$—HCl), 217 (100%) | 11 |
| 60 | H | H | H | Cl | O$^n$Hex | 3-pyridyl | 150~151.5 | 336(M$^+$), 92(100%) | 8 |
| 61 | H | H | H | Cl | O$^n$Hex | 3-pyridyl·HCl | 181~190 | 336(M$^+$—HCl), 217 217(100%) | 11 |
| 62 | H | H | H | Cl | OCH₂Ph | 3-pyridyl·HCl | 164~165 | 342(M$^+$), 251(100%) | 11 |
| 63 | H | H | H | Br | O-cyclopentyl | 3-pyridyl | 222~223 | 364(M$^+$), 92(100%) | 8 |
TABLE II
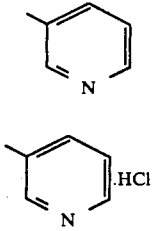
| R₁ | R₂ | R₃ | X | Y | Ar |
|---|---|---|---|---|---|
| H | H | H | Br | OEt | 4-methoxy-1-naphthyl |
| H | H | H | Cl | OMe | 4-methoxy-1-naphthyl |

TABLE II-continued
| R₁ | R₂ | R₃ | X | Y | Ar |
|---|---|---|---|---|---|
| H | H | H | Cl | OEt | 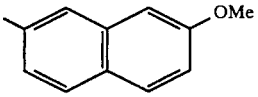 |
| H | H | H | Cl | O^iPr | 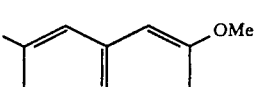 |
| H | H | H | Br | O^iPr | 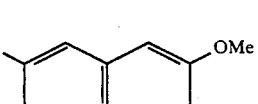 |
| H | H | H | Cl | O^secBu | 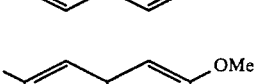 |
| H | H | H | Cl | O^nBu | 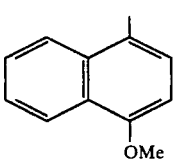 |
| H | H | H | Cl | O^nHex | 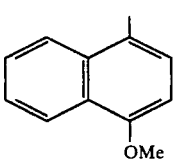 |
| H | H | H | Cl | O^nHep | 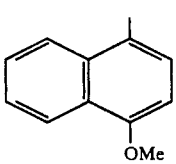 |
| H | H | H | Cl | ^nOct | 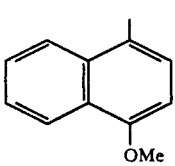 |
| H | H | H | Cl | OEt | 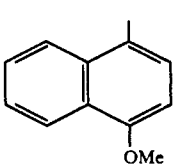 |

TABLE II-continued

[Structure: pyridazinone core with R₁-N-N, X, Y substituents, and N(R₂)-CH(R₃)-Ar side chain]

| R₁ | R₂ | R₃ | X | Y | Ar |
|---|---|---|---|---|---|
| H | H | H | Cl | OⁿPr | 3-Cl-4-OMe-naphthyl |
| H | H | H | Cl | OⁿBu | 3-Cl-4-OMe-naphthyl |
| H | H | H | Cl | OCHPh(Me) | 3-Cl-4-OMe-naphthyl |
| H | H | H | Br | OEt | 3-OEt-4-OMe-naphthyl |
| H | H | H | Br | OⁱPr | 3-OEt-4-OMe-naphthyl |
| H | H | H | Br | OⁿBu | 3-OEt-4-OMe-naphthyl |
| H | H | H | Br | O-cyclopentyl | 3-OEt-4-OMe-naphthyl |
| H | H | H | Br | OCHPh(Me) | 3-OEt-4-OMe-naphthyl |

TABLE II-continued
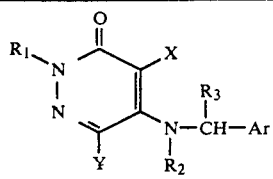
| R₁ | R₂ | R₃ | X  | Y    | Ar |
|----|----|----|----|------|----|
| H  | H  | H  | Br | OMe  | naphthalene with 1-OMe, 2-OⁿPr |
| H  | H  | H  | Br | OEt  | naphthalene with 1-OMe, 2-Me |
| H  | H  | H  | Br | OⁱPr | naphthalene with 1-OMe, 2-Me |
| H  | H  | H  | Br | OⁿBu | naphthalene with 1-OMe, 2-Me |
| H  | H  | H  | Cl | OMe  | naphthalene with 1-OMe, 2-Et |
| H  | H  | H  | Cl | OEt  | naphthalene with 1-OMe, 2-Et |
| H  | H  | H  | Br | SMe  | naphthalene with 1-OMe, 2-Br |
| H  | H  | H  | Br | SMe  | naphthalene with 1-OMe, 2-Br |

TABLE II-continued

| R₁ | R₂ | R₃ | X  | Y            | Ar                                  |
|----|----|----|----|--------------|-------------------------------------|
| H  | H  | H  | Br | S-cyclopentyl | 4-Me, 3-Cl, 1-OMe naphthyl          |
| H  | H  | H  | Br | SCHPh(Me)    | 4-Me, 2-OMe, 1-OMe naphthyl         |
| H  | H  | H  | Br | SEt          | 4-Me, 1-OMe naphthyl                |
| H  | H  | H  | Br | H            | 3-Me, 7-OEt naphthyl                |
| Et | H  | H  | Cl | H            | 3-Me, 7-OEt naphthyl                |
| H  | H  | Me | Br | H            | 3-Me, 7-OEt naphthyl                |
| H  | H  | H  | Cl | H            | 4-Me, 1-OEt naphthyl                |
| H  | H  | H  | Cl | OEt          | 4-Me, 1-OEt naphthyl                |
| H  | H  | H  | Br | O$^i$Pr      | 4-Me, 1-OEt naphthyl                |

TABLE II-continued

Structure:
R₁-N-N=C(Y)-C(=...)-C(X)=C(-N(R₂)-CH(R₃)-Ar)-C(=O) (pyridazinone with N-CH(R₃)Ar substituent)

| R₁ | R₂ | R₃ | X | Y | Ar |
|----|----|----|----|----|----|
| H | H | H | Cl | O^sec Bu | 4-OEt-naphthalen-1-yl |
| H | H | H | Br | O^i Bu | 4-OEt-naphthalen-1-yl |
| H | H | H | Cl | SMe | 4-OEt-naphthalen-1-yl |
| H | H | H | Br | SEt | 4-OEt-naphthalen-1-yl |
| H | H | H | Cl | Cl | 4-OEt-naphthalen-1-yl |
| H | H | H | Br | Br | 4-OEt-naphthalen-1-yl |
| H | H | H | Cl | NO₂ | 4-OEt-naphthalen-1-yl |
| H | H | H | Br | NH₂ | 4-OEt-naphthalen-1-yl |

TABLE II-continued
[structure shown with R1-N(N)-C(=O) pyridazinone core, X, Y, R2, R3, CH-Ar substituents]
| R1 | R2 | R3 | X | Y | Ar |
|---|---|---|---|---|---|
| H | H | Me | Br | O$^i$Pr | 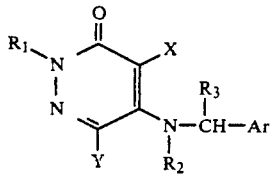 4-OEt naphthyl |
| Et | H | H | Cl | H | 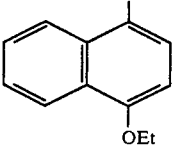 4-OEt naphthyl |
| $^i$Pr | H | H | Br | H | 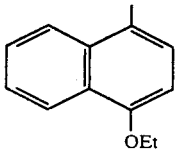 4-OEt naphthyl |
| CH$_2$=CHCH$_2$— | H | H | Br | H | 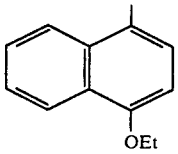 4-OEt naphthyl |
| H | H | H | Cl | OMe | 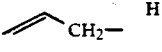 4-O$^n$Pr naphthyl |
| H | H | H | Br | OEt | 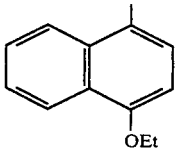 4-O$^n$Pr naphthyl |
| H | H | H | Cl | O$^i$Pr | 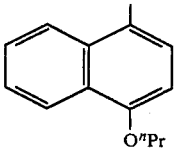 4-O$^n$Pr naphthyl |
| H | H | H | Br | O$^{sec}$Bu | 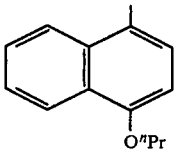 4-O$^n$Pr naphthyl |

TABLE II-continued
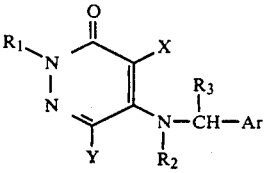
| R₁ | R₂ | R₃ | X | Y | Ar |
|---|---|---|---|---|---|
| H | H | H | Cl | OⁿPr | 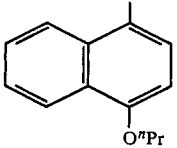 |
| H | H | H | Cl | OEt | 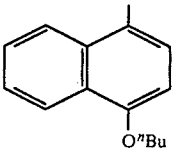 |
| H | H | H | Br | OEt | 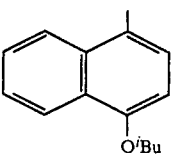 |
| H | H | H | Br | OⁱBu | 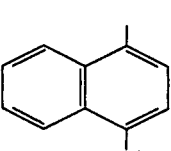 |
| H | H | H | Cl | OEt | 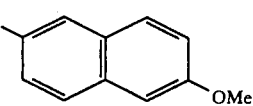 |
| H | H | H | Br | OⁱPr | 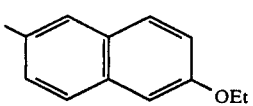 |
| H | H | H | Cl | OEt | 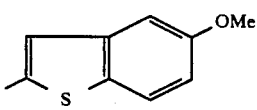 |
| H | H | Me | Br | OⁱPr | 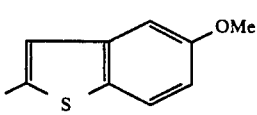 |
| H | H | H | Cl | H | 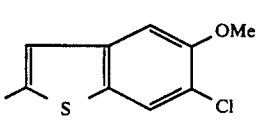 |
| H | H | H | Cl | OMe | 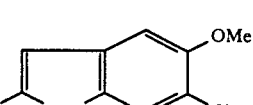 |

TABLE II-continued
| R1 | R2 | R3 | X | Y | Ar |
|---|---|---|---|---|---|
| H | H | H | Cl | OEt | 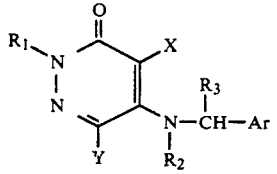 |
| H | H | H | Cl | O$^n$Pr | 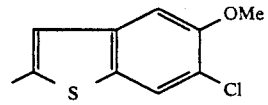 |
| H | H | H | Cl | O$^n$Bu | 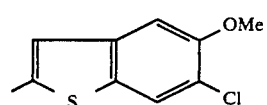 |
| H | H | H | Cl | O$^n$Hex | 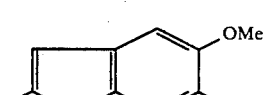 |
| H | H | H | Cl | O$^n$Oct | 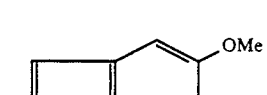 |
| H | H | H | Cl | OEt | 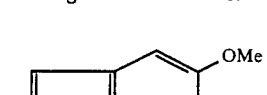 |
| H | H | H | Br | OEt | 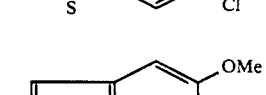 |
| H | H | H | Cl | H | 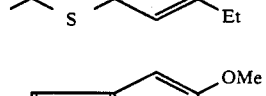 |
| H | H | H | Br | OEt | 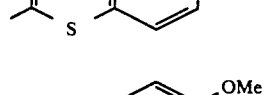 |
| H | H | H | Br | H | 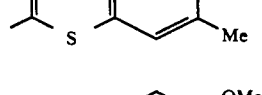 |
| Et | H | H | Br | H | 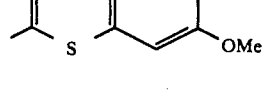 |

TABLE II-continued

| R₁ | R₂ | R₃ | X | Y | Ar |
|---|---|---|---|---|---|
| iPr | H | H | Br | H | thiophene-CH=, aryl = 4,5-di-OMe |
| CH₂=CHCH₂— | H | H | Br | H | thiophene-CH=, aryl = 4,5-di-OMe |
| H | H | H | Cl | H | thiophene-CH=, aryl = 4-OEt, 5-OMe |
| H | H | H | Br | OEt | thiophene-CH=, aryl = 4-OEt, 5-OMe |
| H | H | H | Cl | OiPr | thiophene-CH=, aryl = 4-OEt, 5-OMe |
| H | H | H | Br | Cl | thiophene-CH=, aryl = 4-OEt, 5-OMe |
| H | H | H | Cl | NO₂ | thiophene-CH=, aryl = 4-OEt, 5-OMe |
| H | H | H | Br | SMe | thiophene-CH=, aryl = 4-OEt, 5-OMe |
| H | H | H | Br | OEt | thiophene-CH=, aryl = 4-OnBu, 5-OMe |
| H | H | H | Br | OiPr | thiophene-CH=, aryl = 4-OiBu, 5-OMe |
| H | H | H | Br | Me\|OCHPh | 1-methyl-4-methoxynaphthalene |

TABLE II-continued
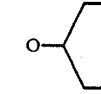
| R₁ | R₂ | R₃ | X | Y | Ar |
|---|---|---|---|---|---|
| H | H | H | Br | 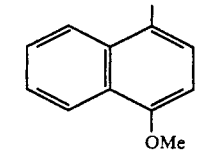 | 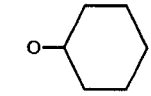 |
| H | H | H | Br | 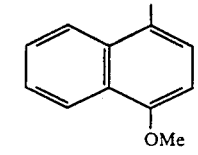 |  |
| H | H | H | Br | 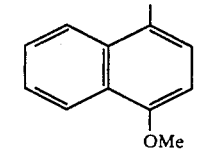 | 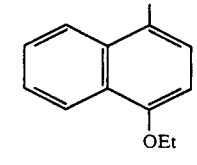 |
| H | H | H | Br | OCH₂Ph |  |
| H | H | H | Br | Me<br>\|<br>OCHPh | 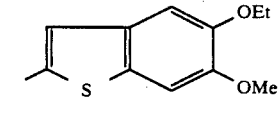 |
| H | H | H | Br | O$^{sec}$Pen | 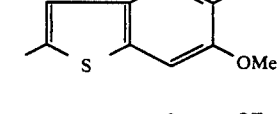 |
| H | H | H | Br | 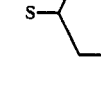 | 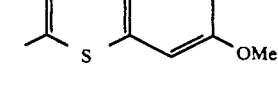 |
| H | H | H | Br | Me<br>\|<br>S—CHPh |  |
| H | H | H | Br | Et<br>\|<br>SCHPh | 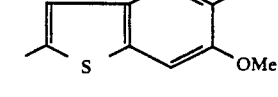 |
| H | H | H | Br | S$^{sec}$Bu |  |

TABLE II-continued
| R₁ | R₂ | R₃ | X | Y | Ar |
|---|---|---|---|---|---|
| H | H | H | Br | H | 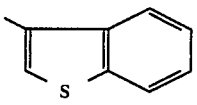 |
| H | H | H | Br | OMe | 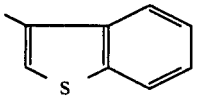 |
| H | H | H | Br | OEt | 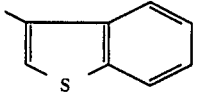 |
| H | H | H | Br | OⁱPr | 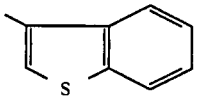 |
| H | H | H | Br | H | 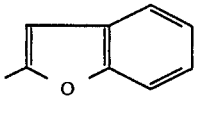 |
| H | H | H | Br | NH₂ | 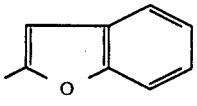 |
| H | H | H | Br | NO₂ | 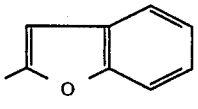 |
| H | H | H | Br | OMe | 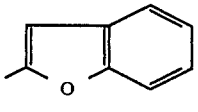 |
| H | H | H | Br | OEt | 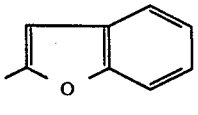 |
| H | H | H | Br | OⁱPr | 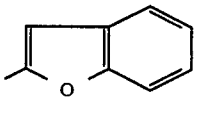 |
| H | H | H | Br | Me<br>\|<br>OCHPh | 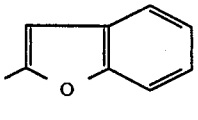 |

TABLE II-continued
| R1 | R2 | R3 | X | Y | Ar |
|---|---|---|---|---|---|
| H | H | H | Br | Cl | 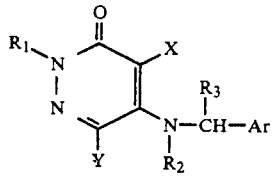 |
| H | H | H | Br | H | 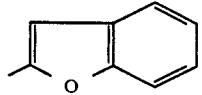 |
| H | H | H | Br | OEt | 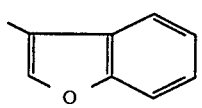 |
| H | H | H | Br | O$^i$Pr | 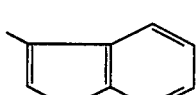 |
| H | H | H | Br | O$^{sec}$Bu |  |
| H | H | H | Br | O-cyclopropyl |  |
| H | H | H | Br | O-cyclopentyl | 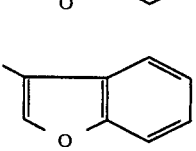 |
| H | H | H | Br | NO$_2$ | 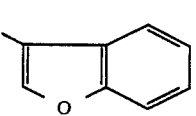 |
| H | H | H | Br | Cl | 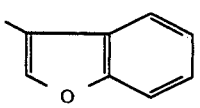 |
| H | H | H | Br | Br | 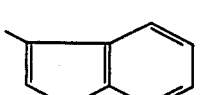 |
| H | H | H | Br | Me\|OCHPh | 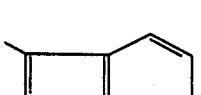 |

TABLE II-continued

Structure: pyridazinone core with R1 on N, =O, X, and N(R2)CH(R3)-Ar substituents, Y group.

| R₁ | R₂ | R₃ | X | Y | Ar |
|----|----|----|----|----|----|
| H | H | H | Br | Et-OCHPh | benzofuran-2-yl |
| H | H | H | Br | SMe | benzofuran-2-yl |
| H | H | H | Br | SEt | benzofuran-2-yl |
| H | H | H | Br | Me-SCHPh | benzofuran-2-yl |
| H | H | H | Br | OEt | 4-Me-thiophen-2-yl (5-Me) |
| H | H | H | Cl | O$^i$Pr | 4-Me-thiophen-2-yl |
| H | H | H | Br | O$^{sec}$Bu | 4-Me-thiophen-2-yl |
| H | H | H | Br | Me-OCHPh | 4-Me-thiophen-2-yl |
| H | H | H | Cl | O-cyclopentyl | 4-Me-thiophen-2-yl |
| H | H | H | Br | O-cyclopropyl | 4-Me-thiophen-2-yl |
| H | H | H | Br | Cl | 4-Me-thiophen-2-yl |
| H | H | H | Br | NO₂ | 4-Me-thiophen-2-yl |

TABLE II-continued

[Structure: pyridazinone core with R₁-N-N, =O, X, Y substituents, and N(R₂)-CH(R₃)-Ar group]

| R₁ | R₂ | R₃ | X | Y | Ar |
|---|---|---|---|---|---|
| H | H | H | Br | OEt | 2-methyl-4-ethylthiophene |
| H | H | H | Br | O$^i$Pr | 2-methyl-4-ethylthiophene |
| H | H | H | Br | O$^{sec}$Bu | 2-methyl-4-ethylthiophene |
| H | H | H | Br | O$^i$Hex | 2-methyl-4-ethylthiophene |
| H | H | H | Cl | OCHPh(Me) | 2-methyl-4-ethylthiophene |
| H | H | H | Br | O-cyclopropyl | 2-methyl-4-ethylthiophene |
| H | H | H | Cl | O-cyclopentyl | 2-methyl-4-ethylthiophene |
| H | H | H | Br | Cl | 2-methyl-4-ethylthiophene |
| H | H | H | Br | NO₂ | 2-methyl-4-ethylthiophene |
| H | H | H | Cl | OEt | 2-methyl-4-$^n$Pr-thiophene |
| H | H | H | Br | OEt | 2-methyl-4-$^i$Bu-thiophene |
| H | H | H | Cl | O$^i$Pr | 2-methyl-4-$^i$Bu-thiophene |

TABLE II-continued
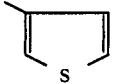
| R1 | R2 | R3 | X | Y | Ar |
|----|----|----|---|---|-----|
| H | H | H | Br | OEt | 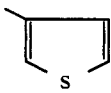 |
| H | H | H | Cl | O$^i$Pr |  |
| H | H | H | Br | O$^{sec}$Bu |  |
| H | H | H | Cl | O$^n$Pr |  |
| H | H | H | Cl | NO$_2$ | 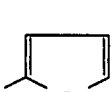 |
| H | H | H | Br | OEt | 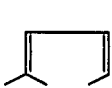 |
| H | H | H | Cl | O$^i$Pr | 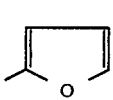 |
| H | H | H | Br | O$^{sec}$Bu |  |
| H | H | H | Cl | Me<br>\|<br>OCHPh |  |
| H | H | H | Br |  |  |
| H | H | H | Cl |  |  |
| H | H | H | Br | OEt |  |

TABLE II-continued
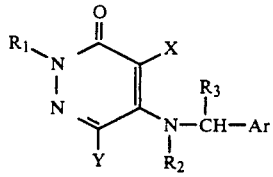
| R₁ | R₂ | R₃ | X | Y | Ar |
|----|----|----|----|----|----|
| H | H | H | Cl | O$^i$Pr | 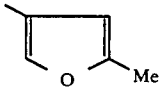 |
| H | H | H | Br | O$^i$Pr | 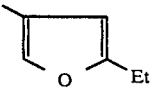 |
| H | H | H | Cl | O$^{sec}$Bu | 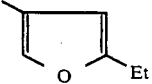 |
| H | H | H | Br | O$^i$Bu | 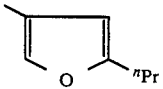 |
| H | H | H | Cl | Cl | 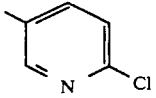 |
| H | H | H | Cl | OEt | 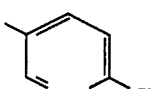 |
| H | H | H | Cl | O$^n$Pr | 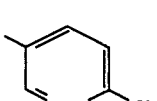 |
| H | H | H | Cl | O$^n$Pen | 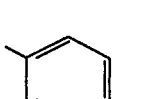 |
| H | H | H | Cl | O$^n$Hex | 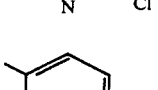 |
| H | H | H | Cl | O$^n$Oct | 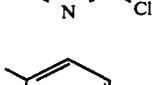 |
| H | H | H | Cl |  | 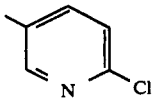 |
| H | H | H | Cl | SEt | 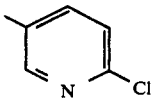 |

TABLE II-continued

Structure: pyridazinone with R1 on N, X, Y substituents, and N(R2)-CH(R3)-Ar group

| R₁ | R₂ | R₃ | X | Y | Ar |
|---|---|---|---|---|---|
| H | H | H | Cl | OCHPh(Me) | 5-methyl-2-chloropyridin-yl |
| H | H | H | Br | OMe | 5-methyl-2-nBu-pyridin-yl |
| H | H | H | Br | OEt | 5-methyl-2-nBu-pyridin-yl |
| H | H | H | Br | O$^n$Pr | 5-methyl-2-nBu-pyridin-yl |
| H | H | H | Br | O$^i$Pr | 5-methyl-2-nPr-pyridin-yl |
| H | H | H | Br | O$^n$Bu | 5-methyl-2-Et-pyridin-yl |
| H | H | H | Br | O$^n$Bu | 5-methyl-2-Me-pyridin-yl |
| H | H | H | Br | OCHPh(Me) | 5-methyl-2-Me-pyridin-yl |
| H | H | H | Cl | O$^i$Pen | 4-methyl-2-nPr-furyl |
| H | H | H | Br | OEt | 4-methyl-2-iBu-furyl |
| H | H | H | Cl | O$^i$Pr | 4-methyl-2-iBu-furyl |

TABLE II-continued
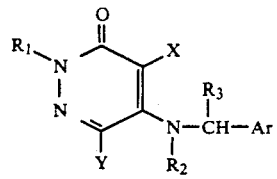
| R₁ | R₂ | R₃ | X | Y | Ar |
|---|---|---|---|---|---|
| H | H | H | Br | OEt | 3-pyridyl |
| H | H | H | Cl | O$^i$Pr | 3-pyridyl |
| H | H | H | Br | OEt | 4-methyl-2-ethoxypyridyl |
| H | H | H | Cl | O$^i$Pr | 4-methyl-2-ethoxypyridyl |
| H | H | H | Br | OEt | 4-methyl-2-(n-butoxy)pyridyl |
| H | H | H | Cl | O$^i$Pr | 4-methyl-2-(n-butoxy)pyridyl |
| H | H | H | Br | OEt | 4-methyl-2-(i-butoxy)pyridyl |
| H | H | H | Cl | O$^i$Pr | 4-methyl-2-(i-butoxy)pyridyl |
| H | H | H | Cl | NO₂ | 7-methylquinolinyl |
| H | H | H | Cl | Cl | 7-methylquinolinyl |

TABLE II-continued

[Structure: pyridazinone core with R1-N-N, Y, X, and N(R2)(R3)-CH(Ar) substituents, C=O]

| R1 | R2 | R3 | X | Y | Ar |
|----|----|----|----|----|----|
| H | H | H | Cl | NH2 | 7-methylquinolin-yl |
| H | H | H | Cl | OMe | 7-methylquinolin-yl |
| H | H | H | Cl | SMe | 7-methylquinolin-yl |
| H | H | H | Cl | OEt | 7-methylquinolin-yl |
| H | H | H | Cl | O<sup>i</sup>Pr | 7-methylquinolin-yl |

Now, Formulation Examples will be given.

| FORMULATION EXAMPLE 1 (Tablets) | |
|---|---|
| Compound No. 31 | 10 g |
| Lactose | 20 g |
| Starch | 4 g |
| Starch for paste | 1 g |
| Magnesium stearate | 100 mg |
| Carboxymethyl cellulose calcium | 7 g |
| Total | 42.1 g |

The above components were mixed in a usual manner, and formulated into sugar-coated tablets each containing 50 mg of an active ingredient.

| FORMULATION EXAMPLE 2 (Capsules) | |
|---|---|
| Compound No. 5 | 10 g |
| Lactose | 20 g |
| Crystal cellulose powder | 10 g |
| Magnesium stearate | 1 g |
| Total | 41 g |

The above components were mixed in a usual manner, and filled into gelatin capsules to obtain capsules each containing 50 mg of an active ingredient.

| FORMULATION EXAMPLE 3 (Soft capsules) | |
|---|---|
| Compound No. 36 | 10 g |
| Corn Oil | 35 g |
| Total | 45 g |

The above components were mixed and formulated in a usual manner to obtain soft capsules.

| FORMULATION EXAMPLE 4 (Ointment) | |
|---|---|
| Compound No. 16 | 1.0 g |
| Olive Oil | 20 g |
| White vaseline | 79 g |
| Total | 100 g |

The above components were mixed in a usual manner to obtain 1% ointment.

| FORMULATION EXAMPLE 5 (Aerosol suspension) | | |
|---|---|---|
| (A) | Compound No. 34 | 0.25 (%) |
| | Isopropyl myristate | 0.10 |
| | Ethanol | 26.40 |
| (B) | A 60-40% mixture of 1,2-dichlorotetrafluoroethane and 1-chloropentafluoroethane | 73.25 |

The above composition (A) was mixed. The solution mixture thereby obtained was charged in a container equipped with a valve, and the propellant (B) was injected from the valve nozzle to a gauge pressure of from about 2.46 to 2.81 mg/cm² to obtain an aerosol suspension.

TEST EXAMPLES

A. Antagonistic activity test against SRS-A

SRS-A is a mixture of $LTC_4$, $LTD_4$, $LTE_4$ and the like. Accordingly, antagonistic activities against SRS-A can be evaluated by one of the following two test methods:

(1) A method of examining the antagonistic activities against SRS-A obtained from a sensitized guinea-pig, (2) A method of examining the antagonistic activities against $LTC_4$, $LTD_4$ or $LTE_4$.

The present inventors examined the antagonistic activities of compounds of the formula I against SRS-A by using the following test methods.

(1) Test methods (1) in vitro test $LTD_4$ antagonism in guinea-pig trachea

Antagonism for $LTD_4$ was determined in isolated male guinea-pig (300–400 g) trachea prepared as spiral strip. Tracheal preparations were suspended under 1 g tension in 10 ml organ baths containing 5 μM of indomethacin and they were incubated for 1 hour prior to used. Contractile responses to $LTD_4$ ($2 \times 10^8$ g/ml) were obtained after the maximal response to histamine ($10^4$ M). Test compounds dissolved in 100% dimethyl sulfoxide were added to the organ baths (final concentration of $10^6$ g/ml) 30 min prior to $LTD_4$ addition, and then contractile responses to $LTD_4$ were compared with those of control which was obtained from a paired trachea in the absence of test compounds. LTD-induced contractions were expressed as a percentage of the maximal response to histamine. The antagonism was determined as follows:

Antagonism (%)=1.0−% contraction in test/% contraction in control)×100

FPL-55712 (Fisons Limited) approved as a selective SRS-A antagonist, was used as the control.

[Structure of FPL-55712]

FPL-55712

(2) in vivo test

Effect on anaphylactic bronchoconstriction mediated by endogeneously liberated SRS-A in passively sensitized guinea-pig Male guinea-pigs (350–450 g) were passively sensitized with intravenous (i.v.) injection of 0.125 ml rabbit anti-EA (egg albumin) serum (Capple Laboratories) 1 to 2 days preceding the experiment. Antigen-induced anaphylactic bronchoconstrictions mediated by endogeneously liberated SRS-A were measured by modified method of Konzett and Rossler (Arch. Exp. Path. Pharmak., 195, 71, 1940). Sensitized guinea-pigs were anaesthetized with intraperitoneal injection of urethane (1.5 g/kg). The right jugular vein was cannulated for the administration of the all agents and trachea was cannulated to record total pulmonary resistance. Guinea-pigs were artificially ventilated by a small animal respirator (Shinano, Model SN-480-7) set at a stroke volume of 4.5 ml and a rate of 50 breaths per min. The change in pulmonary resistance was measured with a pressure transducer (Nihon Kohden, Model TP-602T) connected to a T-tube on the tracheal cannula. The percentage of the maximum bronchoconstriction obtained by clamping off the trachea. Following surgical preparation, the animals were pretreated with indomethacin (2 mg/kg, 10 min), pyrilamine (2 mg/kg, 6 min) and propranolol (0.1 mg/kg, 5 min) prior to the EA challenge (0.2 mg/kg). All test compounds were administered orally 2 hours before the EA challenge. Inhibition (%) of bronchoconstriction was determined as follows: Inhibition (%)=(1.0−% maximum bronchoconstriction in test/% maximum bronchoconstriction in control)×100. The maximum bronchoconstriction was 62±6% (Mean±S.E.M; n=6) and the number of test animals was 5–6.

(2) Test results (1) in vitro test $LTD_4$ antagonisms by test compounds at a concentration of $10^6$ g/ml are shown in Table III.

TABLE III

| Test compound No. | Antagonism Test (%) |
|---|---|
| 5 | 79 |
| 16 | 74 |
| 22 | 39 |
| 23 | 57 |
| 24 | 67 |
| 25 | 50 |
| 30 | 50 |
| 31 | 95 |
| 32 | 50 |
| 34 | 99 |
| 38 | 43 |
| 57 | 69 |
| 60 | 96 |
| FPL-55712 | 94 |

(2) in vivo test

Each of tested 3(2H)pyridazinones of the formula I and pharmaceutically acceptable salts as representative compounds of the present invention showed significant inhibitory effects over the control at a dose of 100 mg/kg by oral administration.

From these results, it is evident that the compounds of the present invention exhibit prominent antagonistic activities against SRS-A and its major constituents $LTC_4$ and $LTD_4$ in vitro and in vivo. Therefore, the compounds of the present invention are expected to be useful as prophylactic and therapeutic drugs against various immediate type allergic diseases such as bronchial asthma, allergic rhinitis, urticaria and hay fever, various inflamatory diseases such as rheumatoid arthritis and spondyloarthritis, or ischemic heart diseases such as angina pectoris and myocardial infarction, induced by SRS-A or by one of $LTC_4$, $LTD_4$ and $LTE_4$ as its constituents or a mixture thereof.

We claim:

1. A 3(2H)pyridazinone of the formula:

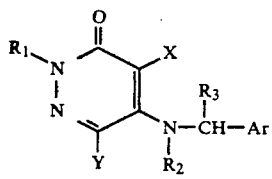
(I)

wherein $R_1$ is hydrogen, 2-propenyl, or straight chained or branched $C_1$-$C_4$ alkyl; each of $R_2$ and $R_3$ which may be the same or different, is hydrogen, or straight chained or branched $C_1$-$C_3$ alkyl; X is chlorine, or bromine; Y is hydrogen, halogen, nitro, amino, or —$AR_4$ wherein A is oxygen, or sulfur, and $R_4$ is hydrogen, straight chained, branched or cyclic $C_1$-$C_8$ alkyl, or

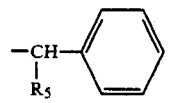

wherein $R_5$ is hydrogen, or straight chained or branched $C_1$-$C_4$ alkyl; and Ar is

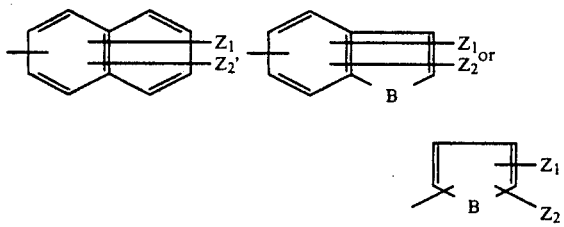

wherein each of $Z_1$ and $Z_2$ which may be the same or different, is hydrogen, halogen, straight or branched $C_1$-$C_4$ alkyl, or —$OR_6$ wherein $R_6$ is straight or branched $C_1$-$C_4$ alkyl, and B is oxygen, sulfur, or —N=C— (to form a quinoline or pyridine ring); or a pharmaceutically acceptable salt thereof.

2. The 3(2H)pyridazinone according to claim 1, wherein Ar is

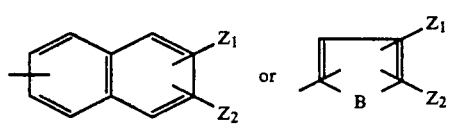

wherein each of $Z_1$ and $Z_2$ which may be the same or different, is hydrogen, halogen, straight chained or branched $C_1$-$C_4$ alkyl, or —$OR_6$ (wherein $R_6$ is straight chained or branched $C_1$-$C_4$ alkyl, and B is oxygen, sulfur, and —N=C— (to form a pyridine ring), or a pharmaceutically acceptable salt thereof.

3. The 3(2H)pyridazinone according to claim 1, wherein $R_3$ is hydrogen, or a pharmaceutically acceptable salt thereof.

4. The 3(2H)pyridazinone according to claim 3, wherein Y is hydrogen, halogen, nitro, amino, or —$OR_4$ wherein $R_4$ is hydrogen, straight chained, branched or cyclic $C_1$-$C_8$ alkyl, or

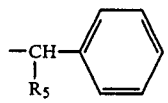

wherein $R_5$ is hydrogen, or straight chained or branched $C_1$-$C_4$ alkyl, or a pharmaceutically acceptable salt thereof.

5. The 3(2H)pyridazinone according to claim 4, wherein $R_2$ is hydrogen, and Y is hydrogen, chlorine, nitro, amino, or —$OR_4$ wherein $R_4$ is straight chained or branched $C_1$-$C_8$ alkyl, $C_3$-$C_6$ cycloalkyl, or benzyl, or a pharmaceutically acceptable salt thereof.

6. The 3(2H)pyridazinone according to claim 5, wherein Ar is

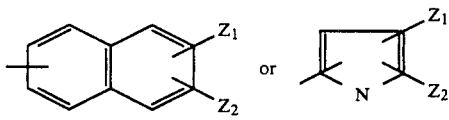

wherein each of $Z_1$ and $Z_2$ which may be the same or different, is hydrogen, chlorine, straight chained $C_1$-$C_4$ alkyl, or —$OR_6$ wherein $R_6$ is straight chained $C_1$-$C_4$ alkyl, or a pharmaceutically acceptable salt thereof.

7. The 3(2H)pyridazinone according to claim 6, wherein Ar is

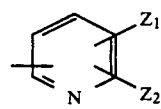

wherein each of $Z_1$ and $Z_2$ which may be the same or different, is hydrogen, chlorine, or —$OR_6$ wherein $R_6$ is straight chained $C_1$-$C_4$ alkyl, or a pharmaceutically acceptable salt thereof.

8. An antagonistic agent against SRS-A comprising an effective amount of a 3(2H)pyridazinone of the formula I as defined in claim 1 or a pharmaceutically acceptable salt thereof and a pharmaceutically acceptable carrier.

* * * * *

UNITED STATES PATENT AND TRADEMARK OFFICE
CERTIFICATE OF CORRECTION

PATENT NO. : 5,011,839

DATED : April 30, 1991

INVENTOR(S) : Keizo Tanikawa et al.

It is certified that error appears in the above-identified patent and that said Letters Patent is hereby corrected as shown below:

Title Page: Item [75] Inventors:

The second inventor's name is incorrect, should be,

--Ryozo Sakoda--.

Signed and Sealed this

Sixth Day of October, 1992

*Attest:*

DOUGLAS B. COMER

*Attesting Officer*     *Acting Commissioner of Patents and Trademarks*